(12) United States Patent
Polak et al.

(10) Patent No.: US 11,400,114 B2
(45) Date of Patent: Aug. 2, 2022

(54) SYNTHETICALLY FUNCTIONALIZED LIVING CELLS FOR TARGETED DRUG DELIVERY

(71) Applicants: Massachusetts Institute of Technology, Cambridge, MA (US); University of North Carolina Chapel Hill, Chapel Hill, NC (US)

(72) Inventors: Roberta Polak, Boston, MA (US); Robert E. Cohen, Jamaica Plain, MA (US); Michael F. Rubner, Westford, MA (US); Elena V. Batrakova, Chapel Hill, NC (US); Matthew J. Haney, Chapel Hill, NC (US); Natalia L. Klyachko, Moscow (RU); Yuling Zhao, Chapel Hill, NC (US)

(73) Assignees: MASSACHUSETTS INSTITUTE OF TECHNOLOGY, Cambridge, MA (US); THE UNIVERSITY OF NORTH CAROLINA AT CHAPEL HILL, Chapel Hill, NC (US)

(*) Notice: Subject to any disclaimer, the term of this patent is extended or adjusted under 35 U.S.C. 154(b) by 0 days.

(21) Appl. No.: 15/458,925

(22) Filed: Mar. 14, 2017

(65) Prior Publication Data
US 2017/0266317 A1   Sep. 21, 2017

Related U.S. Application Data

(60) Provisional application No. 62/308,803, filed on Mar. 15, 2016.

(51) Int. Cl.
*A61K 47/68*   (2017.01)
*A61K 35/15*   (2015.01)
*A61K 38/44*   (2006.01)
*A61K 47/69*   (2017.01)
*A61K 35/28*   (2015.01)

(52) U.S. Cl.
CPC .............. *A61K 35/15* (2013.01); *A61K 35/28* (2013.01); *A61K 38/44* (2013.01); *A61K 47/6815* (2017.08); *A61K 47/6835* (2017.08); *A61K 47/6901* (2017.08); *C12Y 111/01006* (2013.01)

(58) Field of Classification Search
None
See application file for complete search history.

(56) References Cited

U.S. PATENT DOCUMENTS 5,514,670 A * 5/1996 Friedman .............. A61K 9/006
424/185.1
2014/0127774 A1* 5/2014 Swiston ............... C12N 5/0068
435/178

OTHER PUBLICATIONS

Orynbayeva et al., Angew. Chem. Int. Ed. 44: 1092-1096 (2005).*
Batrakova et al., Bioconjugate Chem. 18: 1498-1506 (2007).*
von Büdingen et al, J. Clin. Invest. 122(12): 4533-4543 (2012).*
Doshi et al., Adv. Mater. 23: H105-H109 (2011).*

* cited by examiner

*Primary Examiner* — Erin M. Bowers
(74) *Attorney, Agent, or Firm* — Honigman LLP (57) ABSTRACT

Uniform, functional polymer patches can be attached to a fraction of the surface area of living individual cells. These surface-modified cells can cross the blood-brain barrier while remaining viable after attachment of the functional patch. Functional payloads carried by the patch can include a drug. The patch can include one or more polyelectrolyte multilayers (PEMs).

12 Claims, 10 Drawing Sheets

SYNTHETICALLY FUNCTIONALIZED LIVING CELLS FOR TARGETED DRUG DELIVERY

CLAIM OF PRIORITY

This application claims priority from U.S. Provisional Application No. 62/308,803, filed Mar. 15, 2016, which is incorporated by reference in its entirety.

FEDERALLY SPONSORED RESEARCH OR DEVELOPMENT

This invention was made with government support under Grant No. R01 NS057748 awarded by the National Institutes of Health and under Grant No. DMR-0819762 awarded by the National Science Foundation. The government has certain rights in the invention.

TECHNICAL FIELD

This invention relates to synthetically functionalized living cells.

BACKGROUND

Polyelectrolyte multilayers can be easily assembled on a variety of surfaces. Selection of the materials, assembly conditions, and post-processing conditions can be used to control the chemical, biological, structural and optical properties of the final product. Polyelectrolyte multilayers have previously been used in several biological applications, including drug delivery, biomaterial coatings, and precisely functionalizing surfaces to control adherent cellular growth.

SUMMARY

A composition can include a cell capable of crossing a blood-brain barrier and a polymer patch associated with a fractional portion of the cell surface, where the polymer patch includes a cytophilic layer having a specific affinity for the cell surface and being substantially in contact with the cell surface, an exposed layer, and one or more functional layers intermediate to the cytophilic layer and the exposed layer, wherein the functional layer includes a drug.

In certain embodiments, The cell can be a neutrophil, a monocyte, a macrophage, a mast cell, a dendritic cell, or a mesenchymal stem cell. In certain embodiments, the cell can be a macrophage.

In certain embodiments, the drug can be an enzyme. In certain embodiments, the enzyme can be catalase.

In certain embodiments, the drug can maintain its activity after crossing the blood-brain barrier.

In certain embodiments, the functional layer further can include a magnetic region.

In certain embodiments, the cytophilic layer can include hyaluronic acid, chitosan, biotin, an antibody, or an adhesive peptide. In certain embodiments, the cytophilic layer can include a polyelectrolyte multilayer.

In certain embodiments, the exposed layer can include a polyelectrolyte multilayer.

In certain embodiments, the functional layer can include a polyelectrolyte multilayer. In certain embodiments, the polyelectrolyte multilayer of the functional layer can include poly(allylamine hydrochloride) (PAH).

In certain embodiments, the composition can further include a magnetic layer between the functional layer and the exposed layer.

In certain embodiments, the composition can further include a targeting ligand, wherein the targeting ligand can have an affinity for a blood-brain barrier. In certain embodiments, the targeting ligand includes a peptide, an antibody, or an aptamer.

In certain embodiments, the polymer patch has lateral dimensions in the range of 1 μm to 250 μm and a thickness in the range of 50 nm to 1 μm.

A polymer structure arranged on a substrate can include a labile layer configured to selectively dissociate under predetermined conditions arranged over the substrate-adhering layer, a cytophilic layer arranged over the labile layer, the cytophilic layer having a specific affinity for a surface of a predetermined cell type, where the cytophilic layer has a surface area smaller than a cell of the predetermined cell type, and one or more functional layers arranged intermediate to the labile layer and the cytophilic layer, where the functional layer includes a drug, where the polymer structure includes a targeting ligand, where the targeting ligand has an affinity for a blood-brain barrier.

In certain embodiments, the composition can further include a diffusion barrier layer arranged intermediate to the labile layer and the cytophilic layer.

In certain embodiments, the composition can further include a magnetic layer between the functional layer and the exposed layer.

In certain embodiments, the composition can further include a substrate-adhering layer between the substrate and the labile layer. In certain embodiments, the substrate-adhering layer includes a polyelectrolyte multilayer.

In certain embodiments, the cytophilic layer can include hyaluronic acid, chitosan, biotin, an antibody, or an adhesive peptide. In certain embodiments, the cytophilic layer can include a polyelectrolyte multilayer.

In certain embodiments, the labile layer can include a polymer multilayer.

In certain embodiments, the functional layer can include a polyelectrolyte multilayer. In certain embodiments, the polyelectrolyte multilayer of the functional layer can include poly(allylamine hydrochloride) (PAH).

In certain embodiments, the targeting ligand can include a peptide, an antibody, or an aptamer.

In certain embodiments, the cell can be a neutrophil, a monocyte, a macrophage, a mast cell, a dendritic cell, or a mesenchymal stem cell. In certain embodiments, the cell can be a macrophage.

In certain embodiments, the drug can be an enzyme. In certain embodiments, the enzyme can be catalase.

In certain embodiments, the drug can maintain its activity after crossing the blood-brain barrier.

A method of delivering a drug across a blood-brain barrier can include forming a composition including a cell and a polymer patch associated with a fractional portion of the cell surface, where the polymer patch includes a cytophilic layer having a specific affinity for the cell surface and being substantially in contact with the cell surface, an exposed layer, and one or more functional layers intermediate to the cytophilic layer and the exposed layer, where the functional layer includes a drug, and administering the composition to a subject.

In certain embodiments, the cell can be a neutrophil, a monocyte, a macrophage, a mast cell, a dendritic cell, or a mesenchymal stem cell. In certain embodiments, the cell can be a macrophage.

In certain embodiments, the drug can be an enzyme. In certain embodiments, the enzyme can be catalase.

In certain embodiments, the drug can maintain its activity after crossing the blood-brain barrier.

In certain embodiments, the polymer patch can further include a magnetic layer between the functional layer and the exposed layer.

In certain embodiments, the cytophilic layer can include hyaluronic acid, chitosan, biotin, an antibody, or an adhesive peptide. In certain embodiments, the cytophilic layer can include a polyelectrolyte multilayer.

In certain embodiments, the exposed layer can include a polyelectrolyte multilayer.

In certain embodiments, the functional layer can include a polyelectrolyte multilayer. In certain embodiments, the polyelectrolyte multilayer of the functional layer can include poly(allylamine hydrochloride) (PAH).

In certain embodiments, the polymer patch can have lateral dimensions in the range of 1 µm to 250 µm and a thickness in the range of 50 nm to 1 µm.

In certain embodiments, the composition can further include a targeting ligand, wherein the targeting ligand can have an affinity for a blood-brain barrier. In certain embodiments, the targeting ligand can include a peptide, an antibody, or an aptamer.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1D is an overview of the cell functionalization scheme. Panel (a) shows a regular array of surface-bound patches spaced 50 µm apart. The green fluorescence is from FITC-PAH. Panel (b) shows that after cell incubation and attachment, a majority of the surface-bound patches are occupied. Panel (c) shows that the patches were released from the surface while remaining attached to the cell membrane.

FIGS. 4A-4B show a growth and catalase loading into $(PAH/CAT)_n$ films.

DETAILED DESCRIPTION

Disclosed herein are a method and a system for a targeted drug delivery using layer-by-layer assembly of "cell backpacks." Cellular backpacks are 7-10 µm diameter polymer patches of a few hundreds of nanometers thick that can be fabricated by using layer-by-layer (LbL) assembly onto a photopatterned substrate. See, A. J. Swiston, C. Cheng, S. H. Um, D. J. Irvine, R. E. Cohen, M. F. Rubner, *Nano Lett.* 2008, 8, 4446, A. J. Swiston, J. B. Gilbert, D. J. Irvine, R. E. Cohen, M. F. Rubner, *Biomacromolecules* 2010, 11, 1826, and N. Doshi, A. J. Swiston, J. B. Gilbert, M. L. Alcaraz, R. E. Cohen, M. F. Rubner, S. Mitragotri, *Adv. Mater.* 2011, 23, H105, each of which is incorporated by reference in its entirety. The cell back packs allow for a variety of drugs to be loaded into the payload region. By attaching these backpacks to phagocytes (e.g. macrophages, monocytes, etc.), the cell motility enables a targeted delivery that would not otherwise be achievable and reduce the need for undesirable global dosing of the patient. Most importantly, attachment to macrophages enables the non-invasive delivery of drugs to sites of inflammation, especially across the blood-brain barrier, which is a significant obstacle to drug treatment by traditional means such as systemic administration.

Synthetic materials have been interfaced with biological systems for cellular encapsulation applications. Since at least 1964, encapsulation strategies for cellular cargoes have focused on wrapping a cell or cell aggregate in a protective polymer shell to prevent an autoimmune reaction from deactivating the payload, while allowing small species through the encapsulating semipermeable membrane (see, e.g., Thomas M. S. Chang, *Science* 146 (3643), 524 (1964), which is incorporated by reference in its entirety). Many cell-based therapies, such as those that encapsulate islets cells for diabetes therapy, prefer this immunoisolation approach to systemic immunosupression. See, for example, Gorka Orive, et al., *Nat Med* 9 (1), 104 (2003); Hasan Uludag, et al., *Advanced Drug Delivery Reviews* 42 (1-2), 29 (2000); and Surita R. Bhatia, et al., *Current Opinion in Colloid & Interface Science* 10 (1-2), 45 (2005), each of which is incorporated by reference in its entirety.

Research on polyelectrolyte multilayer encapsulation has primarily focused on uniformly coating the surface of approximately spherical bodies, e.g., living or fixed cells. However, the approaches used restricted the accessibility of the cellular surface to the environment. An approach by which functionality is introduced to a relatively small fraction of a cellular surface (i.e., a "patch") can allow the majority of the cellular surface to remain free to interact with the environment.

Cellular encapsulation strategies have typically completely occluded the surface of the cell from direct contact with its environment. Past efforts have included using polymer multilayer assemblies on the surface of living and dead, fixed cells. See, for example, Matthieu Germain, et al., *Biosensors and Bioelectronics* 21 (8), 1566 (2006); A. Diaspro, et al., *Langmuir* 18 (13), 5047 (2002); S. Krol, et al., *Langmuir* 21 (2), 705 (2005); A. L. Hillberg and M. Tabrizian, *Biomacromolecules* 7 (10), 2742 (2006); S. Moya, et al., *Colloids and Surfaces A: Physicochemical and Engineering Aspects* 183-185, 27 (2001); and R. Georgieva, et al., *Langmuir* 20 (5), 1895 (2004), each of which is incorporated by reference in its entirety.

For cells that elute a species of interest (for example, a metabolite) that can diffuse through a protective membrane, encapsulation may be acceptable. However, for cells that require direct environmental contact to perform their desired functions, these encapsulation strategies can limit the usefulness of such cells. For example, the burgeoning fields of immune system engineering, adoptive T-cell therapies, and advanced cell-based vaccines realize little benefit from the traditional encapsulation paradigm.

Cellular passivation is only one possible option for useful cellular functionalization. For instance, by covering only a portion of a cellular membrane with a functional "patch," cell surface receptors on the rest of the cell membrane can remain free to interact with the environment. For example, poly(diacetylene)-conjugated liposomes can be attached to the cell surface, but many randomly attached nanometer sized "patches" were formed. See, for example, Sofiya Kolusheva, et al., *Angewandte Chemie International Edition* 44 (7), 1092 (2005), which is incorporated by reference in its entirety.

Uniform, multi-functional polymer patches can be attached to cells, and the patches subsequently released from an underlying substrate when exposed to physiological pH conditions and cell-compatible temperatures (e.g., between 4° C. and 37° C.). These engineered heterostructures can include both a "payload" component (such as, for example, superparamagnetic nanoparticles) and a cell-adhesive (i.e. cytophilic) layer that includes a component that has an affinity for the cells in question. For example, in the case of lymphocytes, the cell-adhesive (i.e. cytophilic) layer can include hyaluronic acid. For other cell types, cell-type specific antibodies can be employed to attach the patch to the membrane. The cells can attach to the patch before the patch releases from the surface, thus yielding a synthetically functionalized and living cell. The patches are also referred to as "backpacks," as they share certain characteristics with ordinary backpacks, such as portability, the ability to carry any desired cargo, and can be borne without impairing the functioning of the wearer.

The patches can be attached to various types of cells. In certain embodiments, the patches are conjugated with phagocytes. For examples, the phagocytes can include neutrophils, monocytes, macrophages, mast cells, and dendritic cells. In certain embodiments, the phagocytes can carry the drug-loaded backpacks across the blood-brain barrier as well as into the brains of suitably-challenged subjects (e.g. subjects with inflammatory brain condition). In certain embodiments, the patches can be conjugated with mesenchymal stem cells that can carry the drug-loaded backpacks across the blood-brain barrier and reach the brain.

One method to create the desired patch is with a polyelectrolyte multilayer. In some circumstances, polyelectrolyte multilayers can also confer desirable optical properties to surfaces, such as anti-reflectivity, or reflectivity in a desired range of wavelengths (see, for example, U.S. Patent Application Publication Nos. 2003/0215626 and 2006/0029634), and/or desirable surface energy characteristics. See, for example, U.S. Patent Application Publication Nos. 2006/0029634, which is incorporated by reference in its entirety.

A polyelectrolyte has a backbone with a plurality of charged functional groups attached to the backbone. A polyelectrolyte can be polycationic or polyanionic. A polycation has a backbone with a plurality of positively charged functional groups attached to the backbone, for example poly(allylamine hydrochloride) (PAH). A polyanion has a backbone with a plurality of negatively charged functional groups attached to the backbone, such as sulfonated polystyrene (SPS) or poly(acrylic acid) (PAA), or a salt thereof. Some polyelectrolytes can lose their charge (i.e., become electrically neutral) depending on conditions such as pH. Some polyelectrolytes, such as copolymers, can include both polycationic segments and polyanionic segments.

Layer-by-layer processing of polyelectrolyte multilayers can be used to make conformal thin film coatings with molecular level control over film thickness and chemistry. Charged polyelectrolytes can be assembled in a layer-by-layer fashion. In other words, positively- and negatively- charged polyelectrolytes can be alternately deposited on a substrate. One method of depositing the polyelectrolytes is to contact the substrate with an aqueous solution of polyelectrolyte at an appropriate pH. The pH can be chosen such that the polyelectrolyte is partially or weakly charged, or such that the polyelectrolyte is substantially completely or strongly charged. The multilayer can be described by the number of bilayers it includes, a bilayer resulting from the sequential application of oppositely charged polyelectrolytes. For example, a multilayer having the sequence of layers PAH-PAA-PAH-PAA-PAH-PAA would be said to be made of three bilayers. Each cycle of complimentary polymers produces a complexed, interpenetrated structure referred to as a "bilayer" and the following notation is commonly used: $(Poly_1X/Poly_2Y)_n$. Here, $Poly_1$ and $Poly_2$ refer to the abbreviation for the specific polymers or nanoparticles used in a selected assembly process, X and Y refer to the pH of the solution, and n is the number of bilayers that have been deposited. In some cases, n may be expressed in a decimal notation, such as for example, 3.5, which would indicate that three bilayers of $Poly_1X/Poly_2Y$ were deposited before a final "half-bilayer" of $Poly_1X$ was deposited. In some circumstances, charged nanoparticles can be used to as one or both of the charged species. See, for example, Lee, D., et al., *Nano Letters*, 6, 2305 (2006), which is incorporated by reference in its entirety.

The properties of weakly charged polyelectrolytes can be precisely controlled by changes in pH. See, for example, G. Decher, Science 1997, 277, 1232; Mendelsohn et al., Langmuir 2000, 16, 5017; Fery et al., Langmuir 2001, 17, 3779; Shiratori et al., Macromolecules 2000, 33, 4213; and U.S. patent application Ser. No. 10/393,360, each of which is incorporated by reference in its entirety. A coating of this type can be applied to any surface amenable to the water based layer-by-layer (LbL) adsorption process used to construct these polyelectrolyte multilayers. Because the water based process can deposit polyelectrolytes wherever the aqueous solution contacts a surface, even the inside surfaces of objects having a complex topology can be coated. In general, a polyelectrolyte can be applied to a surface by any method amenable to applying an aqueous solution to a surface, such as dipping or spraying.

Other modifications of a deposited polyelectrolyte multilayer are possible. For example, a nonporous polyelectrolyte multilayer can form porous thin film structures induced by a simple acidic, aqueous process. Tuning of this pore forming process, for example, by the manipulation of such parameters as salt content (ionic strength), temperature, or surfactant chemistry, can lead to the creation of micropores, nanopores, or a combination thereof. A nanopore has a diameter of less than 150 nm, for example, between 1 and 120 nm or between 10 and 100 nm. A nanopore can have diameter of less than 100 nm. A micropore has a diameter of greater than 150 nm, typically greater than 200 nm. Selection of pore forming conditions can provide control over the porosity of the coating. For example, the coating can be a nanoporous coating, substantially free of micropores. Alternatively, the coating can be a microporous coating having an average pore diameters of greater than 200 nm, such as 250 nm, 500 nm, 1 micron, 2 microns, 5 microns, 10 microns, or larger.

Desired chemistries can be included in the polyelectrolyte multilayers. The chemistry can be added during manufacture of the multilayer, or after manufacture. For example, antibacterial chemistries (such as silver nanoparticles or quaternary ammonium salts) can be included in the multilayer during manufacture. The resulting multilayer can then have desired properties (such as antibacterial properties) arising from the incorporated chemistry. In some circumstances, the chemistry can be controllably released from the multilayer.

A patch can be fabricated and functionalized ex vivo. In other words, the patch can be prepared in an environment substantially free of cells. An ex vivo approach can offer more opportunities in geometry, functionalization chemistries, and solvent conditions than does in vivo fabrication.

In general, a patch can have a multilayer structure. Typically the patch is fabricated on a substrate before being introduced to cells. The substrate or patch can optionally include an adhesion layer, depending on the substrate, selected to provide desired mechanical robustness to the patch on the substrate. The next layer is a labile releasable layer. The labile layer is composed of non-cytotoxic polymers. In certain embodiments, the labile layer can include polymers that dissociate in neutral pH conditions, such as H-bonded multilayer films, biopolymers digested by specific enzymes (such as cellulase digestion of cellulose derivatives), hydrolysable polymers, or polymer systems with temperature-dependant solubility (lower critical solution temperature, "LCST", behavior in particular). In certain embodiments, the labile layer can include sugar-mediated disassembly of polymer multilayers. H-bonded multilayer films can include polymers such as poly(acrylic acid) (PAA), poly(methylacrylic acid) (PMAA), poly(ethylene glycol) (PEG), poly(vinylpyrrolidone) (PVPON), poly(N-vinylcaprolactam) (PVCL), and poly(N-isopropylacrylamide) (PNIPAAm). The films can include but are not limited to PAA/PEG, PMAA/PEG, PMAA/PVPON, PMAA/PVCL, or PMAA/PNIPAAm films. In general, the labile layer is selectively removable, under controllable conditions, such that the remaining layers of the patch (described below) are released from the substrate.

The patch can include an optional diffusion barrier, depending on the diffusion characteristics of the functional layer (if present) and of the cytophilic layer. The cytophilic layer includes at least one polymer or other component that has a strong affinity to attach to a cell surface. For example, the cytophilic layer can include extracellular matrix (ECM) polymers (such as hyaluronic acid), or polymers functionalized with adhesive moieties, such as biotin, or adhesive peptides, such as antibodies or RGD-containing peptides. The materials and properties of the cytophilic layer can be chosen to favor attachment of the patch to a desired type of cell. For example, antibodies present in the cytophilic layer can promote attachment of cells bearing the corresponding antigen over cells that do not present the antigen. The cytophilic layer can include reactive groups capable of forming covalent bonds with functional groups on the cell surface. Cell-patch interactions are further discussed below.

In certain embodiments, the patch can include targeting ligands (e.g. peptides, antibodies, aptamers) to decorate the cell-backpack conjugates to help direct the macrophages to the brain.

Figure 1A:
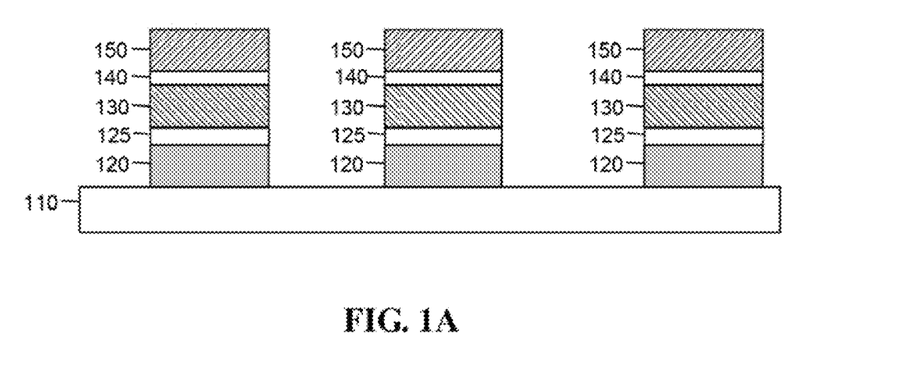
FIGS. 1A-1C are schematic depictions of patches and their associations with cells.

A multilayer patch can be fabricated on a planar surface. Next, cells are introduced, and attach to the outermost cytophilic layer. Last, the labile layer is caused to dissolve or dissociate, an event that can be tuned depending on the nature of the diffusion barrier layer (such as thickness and pH assembly conditions) and environmental conditions such as salinity and temperature. The cells are thus freed from the surface, departing with a polymeric patch attached to its surface. In other words, the cell is partially encapsulated by the patch—only a fraction of the cell surface is covered by the patch. A schematic of this approach is illustrated in FIGS. 1A-1C.

In a modified approach, the patch can be fabricated on a planar surface. The labile layer is next caused to dissolve or dissociate, allowing the patches to float freely. In this free floating state, the patches can be exposed to and become attached to cells.

Figure 1B:
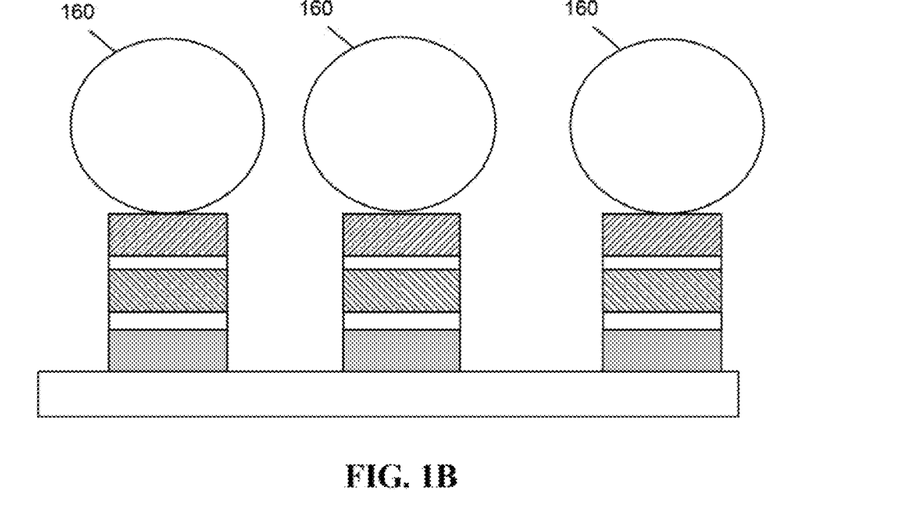
Figure 1C:
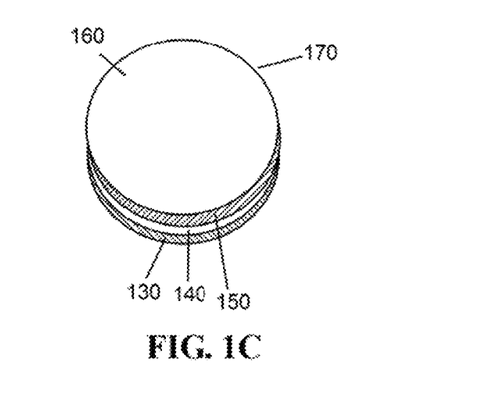
Figure 1D:
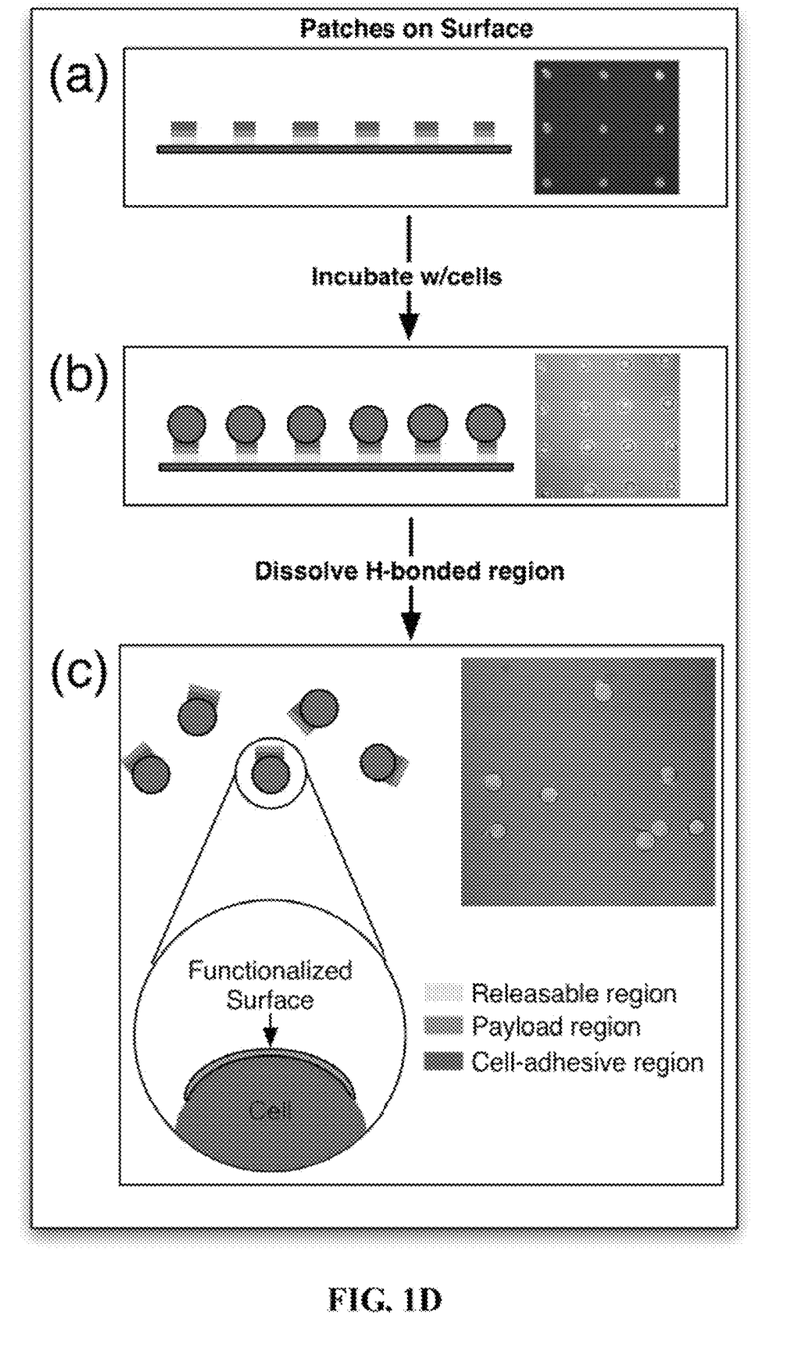

FIGS. 1A-1D illustrate the fabrication of a patch on a substrate, its interaction with a cell, and release of the patch and associated cell from the substrate. Arranged on substrate 110 are three patches, each including an adhesion layer 120, labile layer 125, optional diffusion barrier 130, optional functional layer 140, and cytophilic layer 150. In FIG. 1B, cells 160 are exposed to the patches and individual cells become associated with individual patches via cytophilic layers 150. FIG. 1C illustrates a released cell following dissolution of the labile layer 125. Partially encapsulated cell 160 includes a portion of its surface associated with cytophilic layer 150, optional functional layer 140, and diffusion barrier 130. FIG. 1D presents another overview of cell functionalization with patches.

One method of forming patches is to prepare the desired multilayer assembly on a patterned "stamp," and then transfer this through a process known as polymer-on-polymer stamping, or POPS. POPS is an extension of microcontact printing, which requires the fabrication of a poly(dimethylsiloxane) (PDMS) stamp on which an "ink" is deposited. Inks used in microcontact printing have included small molecules, such as alkanethiols and alkylsiloxanes, as well as higher molecular weight polymers such as PAH. See, for example, Y. Xia, and G. M. Whitesides, *J. Am. Chem. Soc.* 117, 3274 (1995); Y. Xia, et al., *J. Am. Chem. Soc.* 117, 9576 (1995); and M. C. Berg, et al., *Langmuir* 19, 2231 (2003), each of which is incorporated by reference in its entirety.

POPS uses an ink that is an assembled polyelectrolyte multilayers (PEM)—that is, a PEM is built on the patterned PDMS stamp (see, e.g., P. T. H. J. Park, *Advanced Materials* 16, 520 (2004), which is incorporated by reference in its entirety). The stamp is brought into contact with a substrate selected for its ability to interact with the ink. For example, a gold substrate can be used when microcontact printing a thiol-based ink; or a planar substrate coated with another charged polymer in POPS. Specific interactions between the molecules on the PDMS and the substrate can encourage the liftoff of the ink in a complimentary pattern to the relief pattern on the PDMS stamp.

The POPS procedure can be sensitive to aspect ratios of the film thickness and feature diameter. For instance, a film 5 nm thick can easily be stamped with features of approximately 1 μm in size, but a film with a thickness of 50 nm can transfer more effectively if the features are approximately 10 μm in size.

Figure 2:
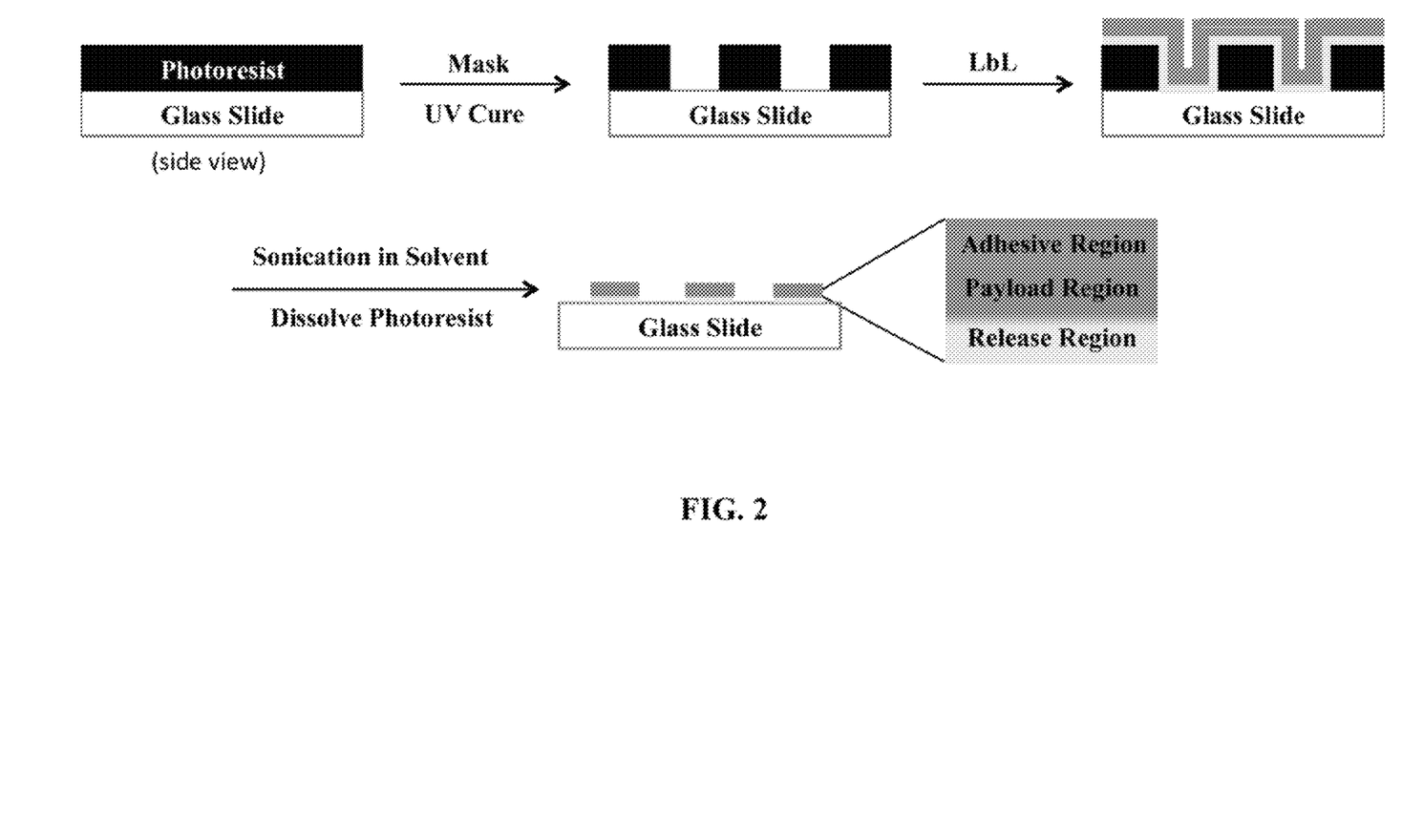
FIG. 2 is a schematic diagram of backpacks fabrication process.

Backpacks can be easily constructed by a combination of photolithography and layer-by-layer assembly. FIG. 2 illustrates the steps involved in the backpacks fabrication. See A. J. Swiston, C. Cheng, S. H. Um, D. J. Irvine, R. E. Cohen, M. F. Rubner, *Nano Lett.* 2008, 8, 4446, which is incorporated by reference in its entirety. First, a glass slide is spin-coated with a photoresist layer. Next, the photoresist is soft-baked to evaporate the solvent and then placed in a custom-made device that holds a photomask and a UV lamp. The parts exposed to the UV lamp are then removed by soaking the glass slide in a developer solution, which can generate a photopatterned slide. The patterned substrate contains circular areas of 7 μm diameter holes and 15 μm edge-to-edge spacing. The next step is to conformally coat the patterned slide with the desired multilayer films using LbL, and dissolve the remaining parts of the photoresist to leave the backpacks attached to the glass slide.

Backpacks can be used for cell-mediated targeted drug-delivery since they can be attached to the surface of living cells without getting internalized. See N. Doshi, A. J. Swiston, J. B. Gilbert, M. L. Alcaraz, R. E. Cohen, M. F. Rubner, S. Mitragotri, *Adv. Mater.* 2011, 23, H105, which is incorporated by reference in its entirety. Recent work demonstrates the ability of backpack-monocyte conjugates to migrate and accumulate in inflamed tissue sites (e.g. lungs and skin). See, A. C. Anselmo, J. B. Gilbert, S. Kumar, V. Gupta, R. E. Cohen, M. F. Rubner, S. Mitragotri, *J. Controlled Release* 2015, 199, 29-36, which is incorporated by reference in its entirety.

Disclosed herein is the use of backpacks attached to macrophages that shows they can migrate across the blood-brain barrier (BBB) in an in vivo model. These backpacks loaded with an enzyme, catalase, can be attached to macrophages via antibody conjugation, and can be used to deliver catalase into the inflamed brain in mice. This demonstrates the use of cell backpacks as a general strategy to deliver pharmaceuticals across the blood-brain barrier (BBB).

The use of macrophages as catalase reservoirs and delivery vehicles to the inflamed brain has been demonstrated previously by internalizing nanoparticles containing the enzyme. See, E. V. Batrakova, S. Li, A. D. Reynolds, R. L. Mosley, T. K. Bronich, A. V. Kabanov, H. E. Gendelman, *Bioconjugate Chem.* 2007, 18, 1498; A. M. Brynskikh, Y. L. Zhao, R. L. Mosley, S. Li, M. D. Boska, N. L. Klyachko, A. V. Kabanov, H. E. Gendelman, E. V. Batrakova, *Nanomedicine* 2010, 5, 379; Y. L. Zhao, M. J. Haney, N. L. Klyachko, S. Li, S. L. Booth, S. M. Higginbotham, J. Jones, M. C. Zimmerman, R. L. Mosley, A. V. Kabanov, H. E. Gendelman, E. V. Batrakova, *Nanomedicine* 2011, 6, 25; X. Yi, D. S. Manickam, A. Brynskikh, A. V. Kabanov, *J. Controlled Release* 2014, 190, 637, and Y. Zhao, M. J. Haney, V. Mahajan, B. C. Reiner, A. Dunaevsky, R. L. Mosley, A. V. Kabanov, H. E. Gendelman, E. V. Batrakova, *J Nanomed Nanotechnol* 2011, S4, each of which is incorporated by reference in its entirety. The use of backpacks is appealing because they can be tailored to carry many different types of enzymes and small molecule drugs. In addition, by tailoring the backpacks with the desired antibodies it is possible to adhere backpacks to a wide variety of cells.

Figure 3:
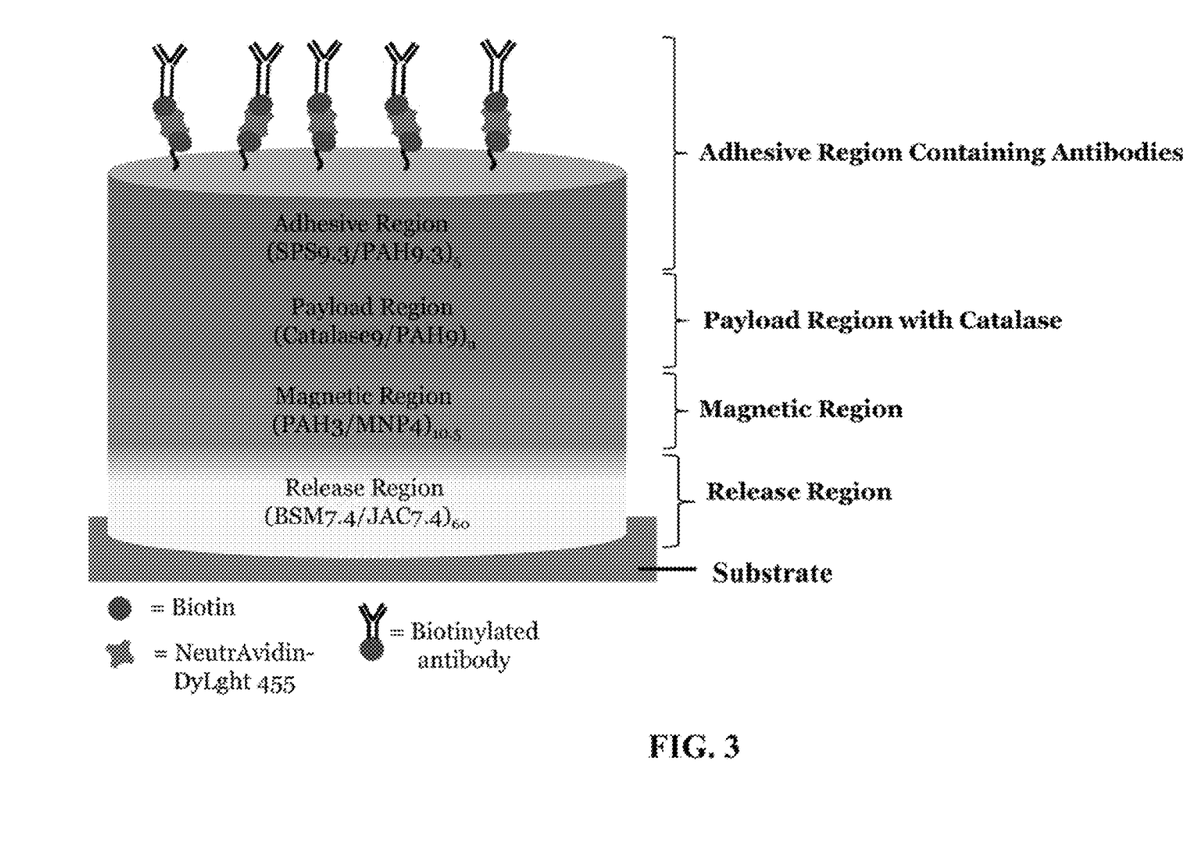
FIG. 3 is a schematic diagram of catalase backpacks.
Figure 9:
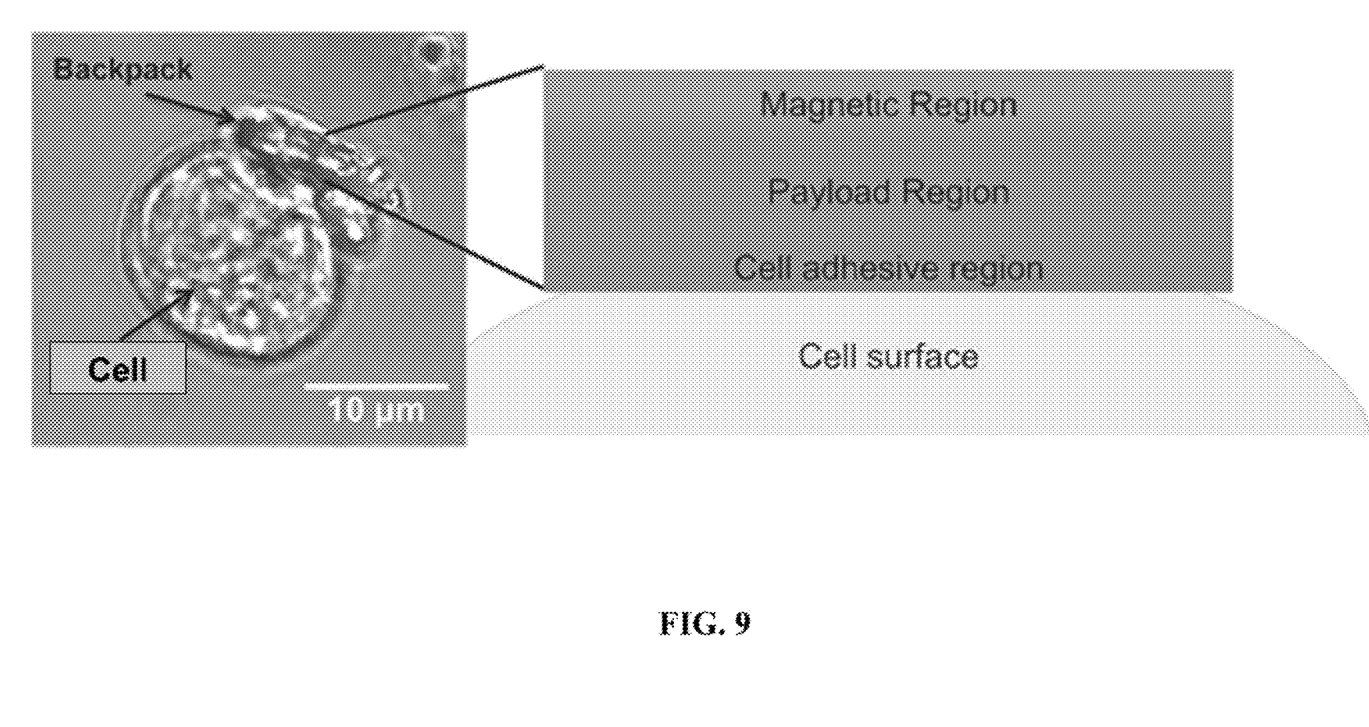
FIG. 9 shows an image and a schematic depiction of a cell-backpack conjugate.

The cell backpacks generally contain multiple sections. FIG. 3 shows a cartoon for the backpacks loaded with catalase, which were used in this work. FIG. 9 shows an image and a schematic representation of a cell-backpack conjugate. The "Adhesive Region" is a cytophilic layer that enables the backpacks to specifically attach to the desired cell through specific antigen binding. The "Payload Region" is a functional layer that contains the desired therapeutic. Functional payloads carried by the patch may include, for example, drugs or other small molecules, peptides, proteins, thermally responsive polymers, and nanoparticles, or any other material that can be incorporated in a polymer patch of subcellular dimensions. In this specific formulation, it is loaded with the enzyme catalase. The "Magnetic Region" aids in purification of cell backpacks and confers film rigidity. The "Release Region" can be a substrate-adhering layer and can dissolve upon incubation with the sugar, melibiose, as a simple means to releasing the backpacks from the glass slides for attachment to cells. In certain embodiments, there can be a separate substrate-adhering layer between the substrate and the "Release Region."

TABLE 1

Description of the polymers and other materials used in the Backpack fabrication.

| Acronym | Full name | Function |
| --- | --- | --- |
| BSM | Bovine Submaxillary Mucin | Glycoprotein |
| JAC | Lectin Jacalin | Carbohydrate-binding protein |
| PAH | Poly(allylamine hydrochloride) | Polycation |
| MNP | Magnetic nanoparticles | Negatively magnetic nanoparticles used for separation in magnetic columns |
| Catalase | — | Antioxidant enzyme |
| NHS-Biotin | N-hydroxysuccinimidobiotin | Reacted to the free amine groups of PAH (top layer) for the conjugation of NeutrAvidin on the backpack surface |
| SPS | Poly(styrene 4-sulfonate) | Polyanion |
| NeutrAvidin | — | Used for the conjugation of a biotinylated antibody on the Backpack surface |
| DyLight 455* | — | |
| Biotinylated antibody** | — | Used to selectively anchor the Backpack on the cell surface |

*Other wavelengths can be used.
**Specific antibodies can be used for different cell types.

In certain embodiments, surface functionalization can be done by providing non-native abilities to the cells by virtue of the associated patches. In one example, during PEM fabrication, magnetic nanoparticles can be incorporated into the layers, and once the final polymer patch is attached to the surface of the cell, the cells responded to an applied magnetic field. Any number of functional materials, including (but not limited to) magnetic and environmentally-responsive materials, drugs, or imaging contrast agents, can be included in a patch. The corresponding function can thus be provided to cells, without requiring the cells to internalize the functional materials of interest.

An in vivo method can functionalize the surface of a living cell. A PEM film is stamped directly onto the cell surface without first fabricating a patch as described above. This can be accomplished by using a modified POPS protocol, similar to what has been used to fabricate Janus-style capsules (see, e.g., Z. Li, *Macromolecules* 38, 7876 (2005), which is incorporated by reference in its entirety. A cytophilic, HA-terminated PEM can be assembled on a patterned or unpatterned PDMS stamp. This PDMS stamp is then lowered onto a monolayer of adherent cells, either densely packed or ordered into a 2D periodic structure (see, e.g., H. Kim, *Advanced Functional Materials* 16, 1313 (2006), which is incorporated by reference in its entirety).

After PEM deposition onto the cell surface, well-established chemistries, such as EDC/NHS (1-ethyl-3-(3-dimethylaminopropyl) carbodiimide hydrochloride/N-hydroxysuccinimide), can be used to functionalize the PEM film in addition to any functionalization added during the PEM deposition process (that is, during PEM film fabrication).

Nearly all cell types bear free thiol (—SH) groups on the cell surface. Thiol groups can react with other functional groups (such as, e.g., a maleimide group) and this reactivity can be used to form a covalent bond between a patch and the cell surface. In particular, a patch may be exposed to a crosslinking reagent prior to be exposed to cells. The crosslinking reagent can be chosen to have two reactive groups with differing reactivity, so that one reactive group can form a covalent bond with a functional group found in the patch, and the other reactive group can form a covalent bond with a thiol group. For example, the crosslinking reagent can include an amine-reactive functional group (such as, for example, an N-hydroxysuccinimide group, capable of reacting with amine groups in, for example, PAH) and a thiol reactive group. Other suitable reactive groups and crosslinking reagents are known. For examples, the crosslinking reagents such as N-[κ-maleimidoundecanoyloxy]sulfosuccinimide ester (sulfo-KMUS) and succinimidyl-[(N-maleimidopropionamido)-octaethyleneglycol] ester (SM(PEG)$_8$) can be used (both available from Pierce Biotechnology). Other crosslinking reagents are commercially available, from Pierce and other suppliers.

A covalent linking approach was used to associate patches with dendritic cells, another type of immune cell. Dendritic cells belong to a large class of cells called antigen-presenting cells, or APCs, which are known to be phagocytotic. In general, these cells can internalize and digest anything found in their environment, presenting fragments of resulting antigens on their surface, in turn stimulating further immune system responses.

Unlike nano- or microparticle based delivery systems, these phagocytes did not internalize the patches. Cells were observed with patches attached, then being released from the cell surface, and then being picked up again. Cells with patches attached were also observed to phagocytose small polystyrene beads, demonstrating that the cell was still able to perform its native function (phagocytosis) without interference from the patch. It also demonstrated that the patch can remain exposed to the extracellular environment and able to deliver drug, adjuvants, or antigens to the local surroundings while the cell remains able to phagocytose and process antigens for presentation.

In certain embodiments, targeting ligands, such as peptides, antibodies, aptamers, can be used to decorate the cell-backpack conjugates to help direct the macrophages to the brain.

The use of cell backpacks attached to macrophages demonstrates a significantly less invasive approach to delivering drugs to the brain. Furthermore, this does not require any additional treatments that permeabilize the blood-brain barrier.

Existing cell-based therapies using macrophages as delivery vehicles use the phagocytosis to internalize particles containing the desired cargo. This methodology presents a problem because as soon as the nanoparticle containing the drug is internalized, degradation of the drug starts inside the lysosome. In this case, cell backpacks present a great advantage compared to those methods as backpacks are adhered outside the cell, and therefore the drug is protected from degradation for longer times. It can also present an advantage while carrying toxic drugs outside the cell versus inside the cell.

Backpacks loaded with different types of cargo (e.g. enzymes, antibiotics, anti-inflammatories, anticancer drugs) can be conjugated to the surface of living cells (e.g. macrophages, lymphocytes, monocytes). The cell-backpack conjugate is then used as targeted drug-delivery system, since cell motility enables a targeted delivery that would not otherwise be achievable. Most importantly, attachment to macrophages enables the non-invasive delivery of drugs to sites of inflammation, especially across the blood-brain barrier, a significant obstacle to drug treatment by traditional means such as systemic drugs. The cell-backpack conjugates can also be used for theranostic cargos, when carrying diagnostic cargos (e.g. imaging purposes) and therapeutic cargos at the same time.

EXAMPLES

Antibody Attachment

Backpacks are reacted with 5 mM of NHS-biotin in a pH 7.4 PBS buffer for 2 hours at room temperature. Samples were rinsed thrice in PBS and reacted with 50 µg/mL NeutrAvidin Dylight 633 in pH 7.4 PBS buffer for 1 hour at 4° C. Glass slides are rinsed three times in PBS. Backpacks are then incubated with biotinylated antibody (50 ug/mL) diluted with PBS buffer (pH 7.4) for 1 hour at room temperature in pH 7.4 PBS buffer, followed by three rinse steps to remove the non-reacted antibody. See, R. Polak, T. Crouzier, R. M. Lim, K. Ribbeck, M. M. Beppu, R. N. M. Pitombo, R. E. Cohen, M. F. Rubner, *Biomacromolecules* 2014, 15, 3093, which is incorporated by reference in its entirety.

Release of Cell-Backpacks Conjugates Directly From the Glass Slide

Cell incubation protocol example can be found in previous publications. See, A. J. Swiston, C. Cheng, S. H. Um, D. J. Irvine, R. E. Cohen, M. F. Rubner, *Nano Lett.* 2008, 8, 4446, and F. C. Vasconcellos, A. J. Swiston, M. M. Beppu, R. E. Cohen, M. F. Rubner, *Biomacromolecules* 2010, 11, 2407, each of which is incorporated by reference in its entirety. Briefly, the slide is cut and placed in the bottom of a well in a 6-well plate or a small Petri dish. 2 mL of cells suspended in appropriate media ($\sim10^6$ cells/mL) are pipetted onto the surface. The entire plate is agitated for 15 minutes at 37° C., followed by 37° C. incubation for 15 minutes, and this cycle is repeated identically once more. The glass slide, now containing cells attached to surface-bound patches, is removed and gently shaken for ~15 s upside down in 37° C. PBS to remove all cells not attached to a patch.

In this case, to release the cell-backpacks, 1 mL of 100 mM of melibiose in PBS was added to the top of the glass slide and incubated for 1 hour at 37° C. These solutions were then pipetted up and down to release the cell-backpacks from the glass slide. See, Polak et al, *Biomacromolecules*, 2014, 15 (8), pp 3093-3098, which is incorporated by reference in its entirety. Additionally a cell scraper is used to help remove the cell-backpack conjugates from the glass slide.

Transport of Backpacks-Loaded Macrophages Across the BBB in Vitro Chemotaxis System The ability of drug-loaded macrophages to cross the BBB under inflammatory conditions is evaluated with an in vitro model of brain inflammation that allows for fast screening of several pre-selected formulations. See A. M. Brynskikh, Y. Zhao, R. L. Mosley, S. Li, M. D. Boska, N. L. Klyachko, A. V. Kabanov, H. E. Gendelman, E. V. Batrakova, *Nanomedicine (Loud)* 2010, 5, 379, which is incorporated by reference in its entirety. Macrophage chemotactic factor-one (MCP-1) can be used to mimic inflammation in the brain. To construct an in vitro BBB model, mouse brain endothelial cells (bEnd.3) are seeded on 24-well polycarbonate membrane inserts and cultured until confluency (typically, in 12 days). This BBB in vitro model was established and used routinely to examine various drug delivery systems for CNS delivery. Loaded with fluorescently-labeled backpacks, macrophages are added in the upper chamber of bEnd.3 monolayers ($1.5\times10^5$ cell/well). Macrophages can be also labeled with Alexa Fluor Protein Labeling Kit (Invitrogen) to trace the cell migration separately. Chemo-attractant, MCP-1 (150 ng/ml, R&D Systems), is placed into the lower chamber. See M. L. Zelivyanskaya, J. A. Nelson, L. Poluektova, M. Uberti, M. Mellon, H. E. Gendelman, M. D. Boska, *J Neurosci Res* 2003, 73, 284, which is incorporated by reference in its entirety. Following various times (1-6 hours), the bEnd.3 inserts are removed, placed in 24-well plates and centrifuged to pellet the migrating cells. The cells are then lysed, and the amount of labeled particles and cell-carriers is measured by fluorescence. See, E. Batrakova, S. Li, V. Alakhov, D. Miller, A. Kabanov, *J Pharmacol Exp Ther* 2003, 304, 845, which is incorporated by reference in its entirety. The data is expressed as % transported material or the cell-carriers±SEM (n=3) and plotted against the time. The apparent permeability coefficients ($P_{app}$) are calculated as follows: $P_{app}=(V1AC_0) \times dC/dt$ (cm/s), where $V \times dC/dt$ is the steady-state rate of drug appearance at the abluminal side, $C_0$ is the initial drug amount in backpacks-loaded macrophages, and A is the surface area of the membrane. The backpack-loaded macrophages that demonstrate considerable transport across BBB can be selected for the further in vivo evaluations.

Figure 8:
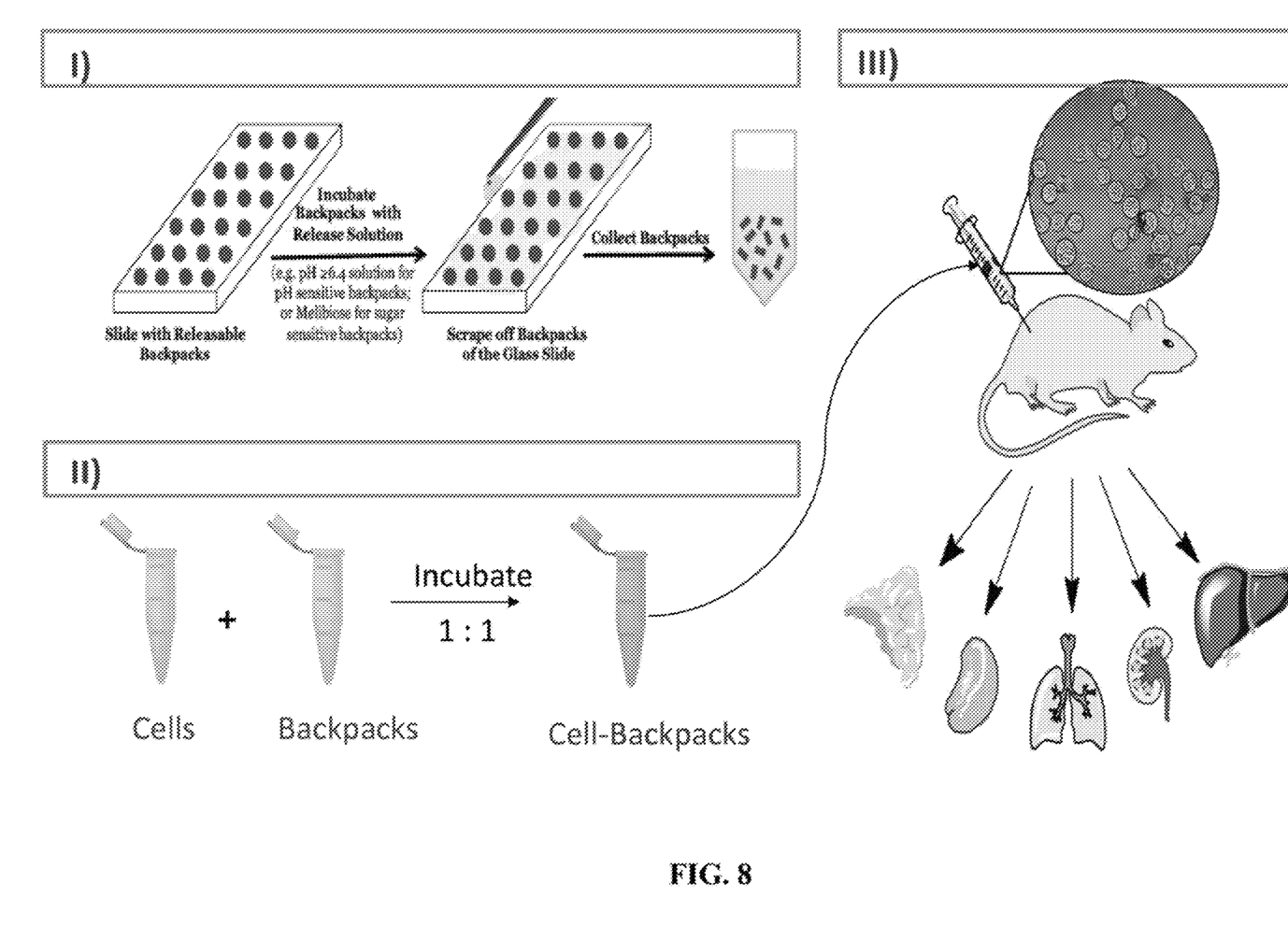
FIG. 8 shows a schematic diagram of an in vivo experiment.

Tracking of Backpack-Loaded Macrophages into SNpc and Striatum of Mice with Brain Inflammation To assess the ability of pre-loaded macrophages to migrate to the brain, image visualization and infrared spectroscopy (IVIS) studies are carried out. See, Y. Zhao, M. J. Haney, V. Mahajan, B. C. Reiner, A. Dunaevsky, R. L. Mosley, A. V. Kabanov, H. E. Gendelman, E. V. Batrakova, *J Nanomed Nanotechnol* 2011, S4, and A. M. Brynskikh, Y. Zhao, R. L. Mosley, S. Li, M. D. Boska, N. L. Klyachko, A. V. Kabanov, H. E. Gendelman, E. V. Batrakova, *Nanomedicine (Loud)* 2010, 5, 379, each of which is incorporated by reference in its entirety. C57BL/6 mice are stereotactically intoxicated with 6-hydroxidophamine (6-OHDA) into SNpc to produce brain inflammation. Then labeled backpack-loaded macrophages are administered i.v. to PD mice ($5 \times 10^6/100$ μl/mouse) 21 days after the intoxication (at the peak of inflammation). See FIG. 8 for a schematic representation of this procedure. The control group receives labeled backpacks alone. Healthy animals without brain inflammation are also used as another control group. All treatment solutions are injected at the same level of fluorescence. For auto-fluorescence evaluations, all animals are imaged before the injections and at different time points (1-30 days) post-treatment in the IVIS 200 Series imaging system. For in situ characterization, brains of the treated mice are sliced and stained with specific markers for different cell types. In particular, the brain slides can be co-stained with: primary (1) rabbit polyclonal antibodies to neurons, AntiNeuN (ab128886, Abcam, 1:500 dilution), or (2) anti-tyrosine hydroxylase (TH) rabbit antibodies to TH-neurons (Calbiochem, 1:1000 dilution), or (3) rabbit anti CD146 to endothelial cells (ab75769, Abcam, 1:250 dilution), or (4) rabbit anti-GFAP antibodies to astrocyte marker (ab7260, Abcam, 1:500 dilution), and secondary antibodies, donkey anti-rabbit IgG H&L Alexa 555 (abcam ab150074, Abcam, 1:500dilution). All slides are permeabilized for 60 min in 0.1M citrate buffer pH6.0 and 0.05% Tween 20, washed 3×5 min with 0.05% Tween 20 in PBS, blocked for 30 minutes with PBS and 5% Normal Donkey Serum+0.05% Tween 20, and stained with primary antibodies at stated dilution overnight at 4 C. Following the incubation, slides are washed 3×5 minutes/wash in PBS/Tween, and stained with secondary antibodies for one hour at room temperature. Then, the slides are washed 3×PBS/Tween 5 min/wash with ddH$_2$O, and covered using Vectashield Hardset mounting media with DAPI. The images can be examined by a confocal fluorescence microscopic system ACAS-570 and corresponding filter set. A summary of all experimental groups for IVIS experiments is outlined in Table 2.

TABLE 2

Summary of experimental groups for IVIS studies.

| Animal group | Experimental Treatment | Purpose for the group |
| --- | --- | --- |
| 6-OHDA mice | Labeled backpacks with cells | Evaluate effect of macrophage transport |
| 6-OHDA mice | Labeled backpacks alone | Assess benefits of cell-mediated transport |
| Healthy mice | Labeled backpacks with cells | Evaluate effect of brain inflammation |

Figure 7:
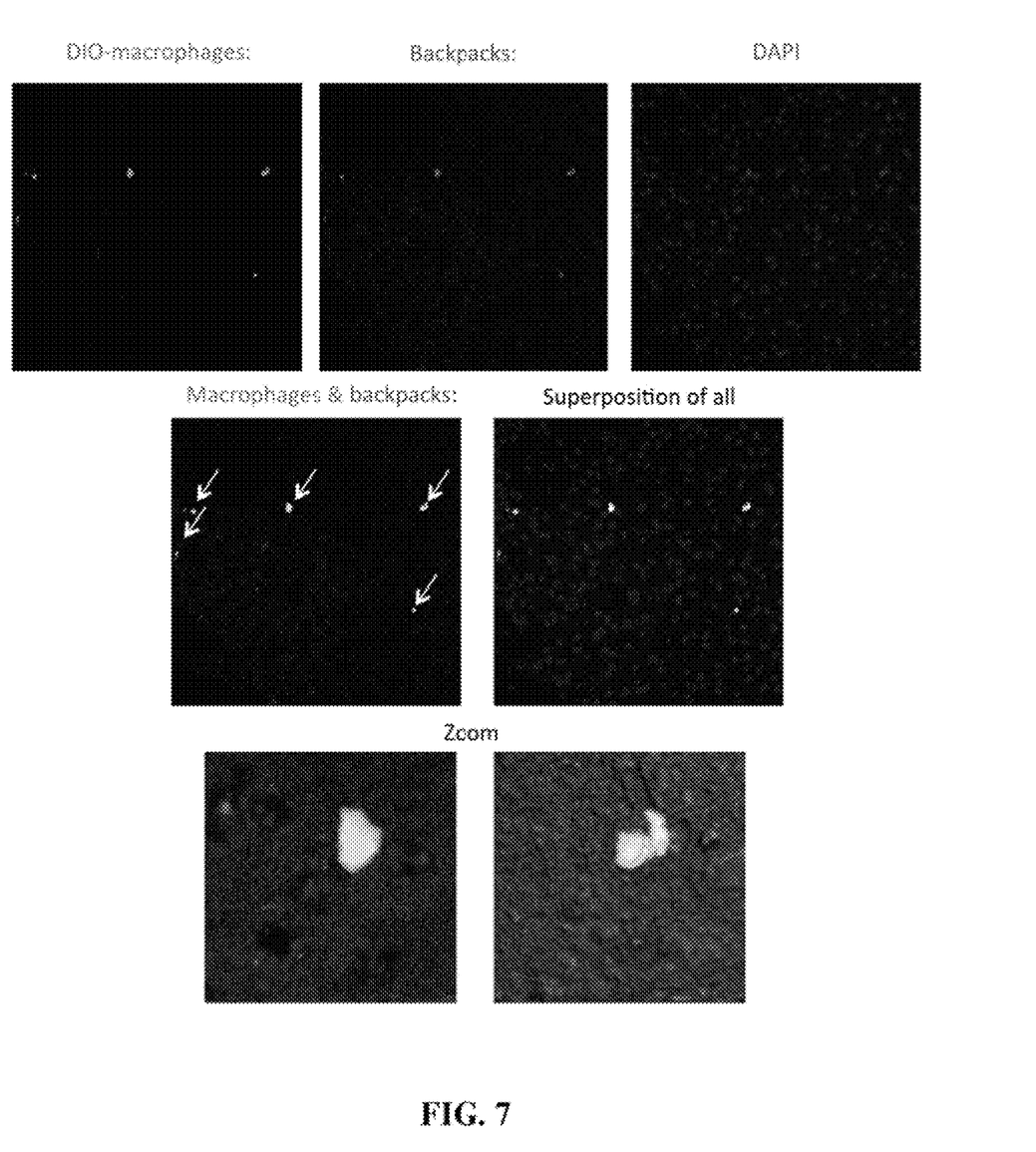
FIG. 7 shows confocal fluorescent images of sectioned mouse brain showing the colocalization of macrophages (green) and cell backpacks (red).

Recruitment of Macrophages with the Attached Backpacks to SNpc in LPS-Intoxicated Mice Fluorescently-labeled DIO-macrophages (green, $2 \times 10^6$ cells/ml) were pipetted onto the surface of the glass slide with fluorescently-labeled backpacks (red) attached. To label backpacks, NeutrAvidin 555 was used. The glass slide, containing cells attached to surface-bound patches was washed 3× with media to remove all cells not attached to a patch. 1 mL of 100 mM of melibiose in PBS was added to the plate on top of the glass slide and incubated for 1 hour at 37° C. in the incubator to release the backpacks from the glass. Cells with the attached backpacks were removed with cell scraper and re-suspended in the saline buffer. C57BL/6 mice were i.c. intoxicated with lipopolysaccharides (LPS, (10 μg LPS in 0.9% NaCl with 0.02% ascorbic acid) into SNpc (flow rate of 0.1 μL/min into the striatum, AP: +0.5; L: −2.0 and DV: −3.0 mm). Twenty four hours later, the animals were i.v. injected with macrophages with attached backpacks ($5 \times 10^6$ cells/mouse in 100 μl). Fourteen hours later, mice were sacrificed, and perfused with PBS and 4% PFA. Brains were frozen, sectioned with a cryostat (10 μm thick), and examined by confocal microscopy (60× magnification). LPS-intoxicated mice injected with backpacks alone (no cells) were used as a control group. Co-localization of fluorescently-labeled macrophages (green) and backpacks (red) manifested in yellow staining (shown by arrows) confirmed that macrophages delivered considerable amount of backpacks to the inflamed brain. No fluorescence was found in the inflamed brain when backpacks were injected alone (without cells) indicating that systemically administered macrophages accomplished transport of backpacks cross the BBB in the presence of brain inflammation (FIG. 7; the bar is 20 μm).

Catalase Loading and Activity.

Figure 4A:
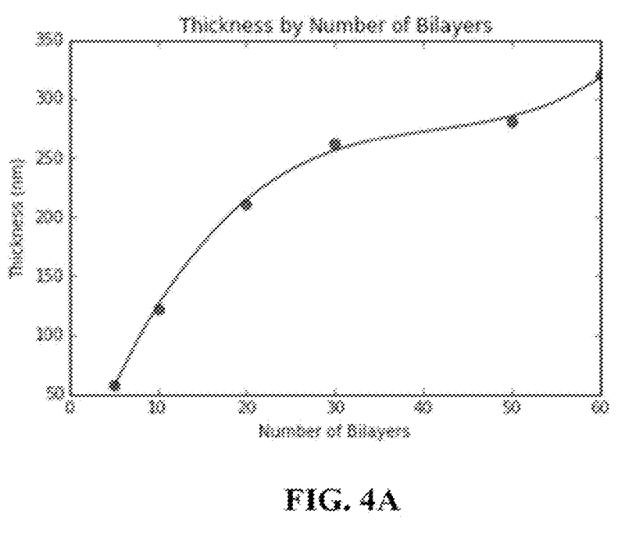
FIG. 4A shows a film growth curve.
Figure 4B:
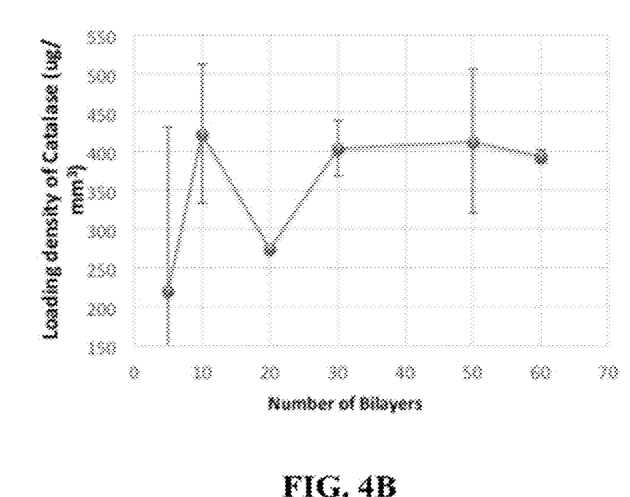
FIG. 4B shows a catalase content.

The growth behavior of LbL assembled (PAH/CAT)$_n$ films were examined to ensure significant quantities of catalase (CAT) can be loaded into the films. In FIG. 4A shows that the film initially grows rapidly up to 30 bilayers after which the amount of material deposited per layer is reduced. During film assembly, the catalase loading density (FIG. 4B) remains significant, stabilizing at roughly 400 ug/mm$^3$ above 30 bilayers.

Figure 5:
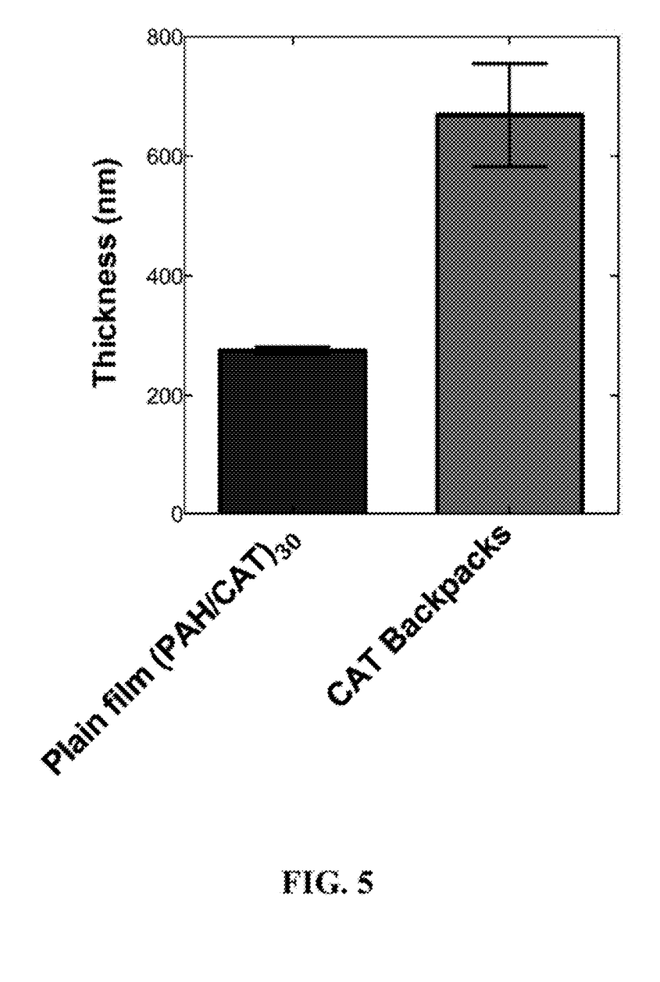
FIG. 5 shows a film thicknesses.

When assembling the cell backpacks, (PAH/CAT)$_{30}$ was used as the payload region (FIG. 2). As shown in FIG. 5, it comprises of nearly a third of the overall thickness of the cell backpacks. The catalase activity in the backpacks were 53±20 μU/BP and found them to still be active after a month after their fabrication (the theoretical activity base on catalase loading/BP is ~83.4 μU/MP).

Ability for Backpacks to Cross the Blood Brain Barrier In Vitro

Figure 6:
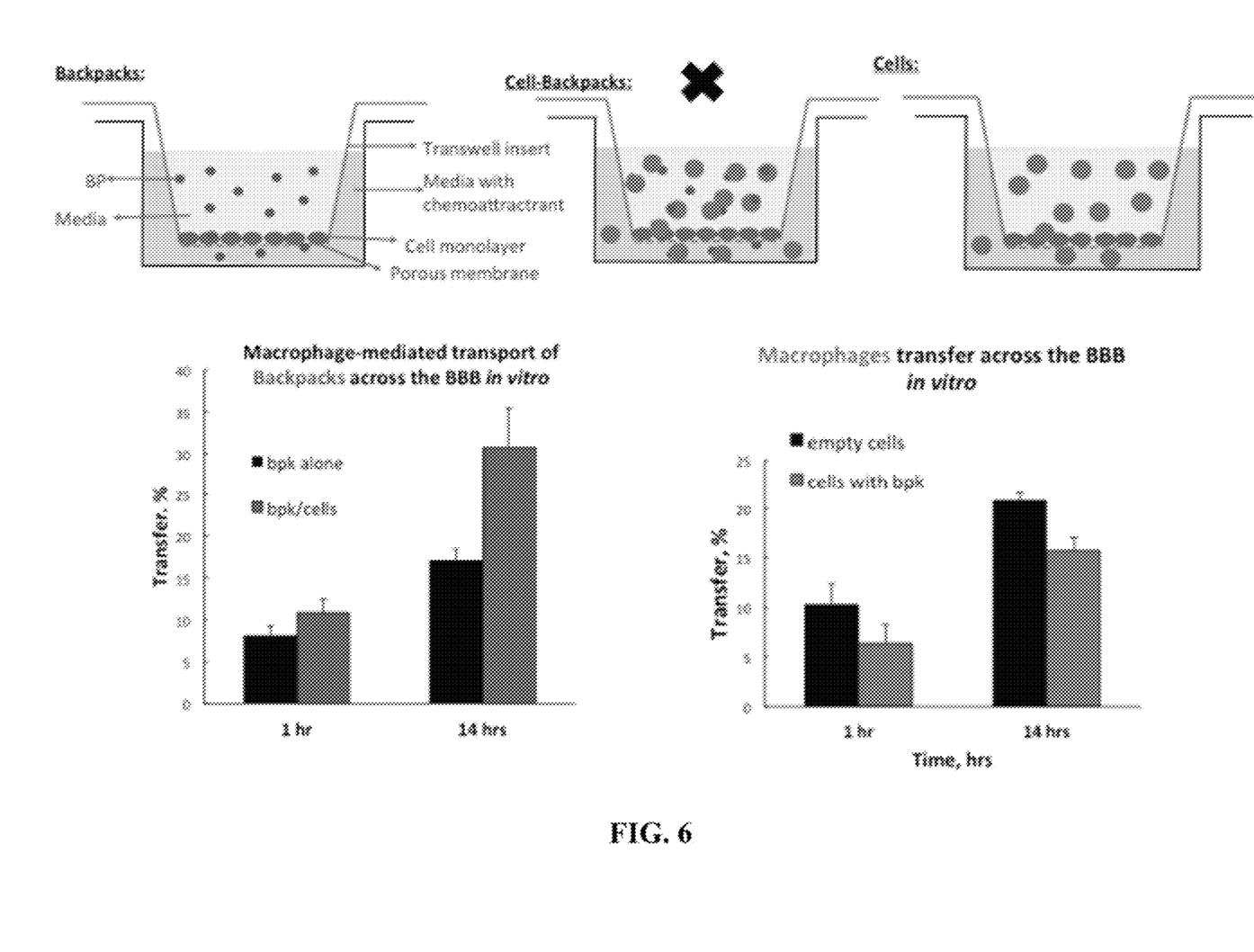
FIG. 6 shows in vitro assay of the translocation of macrophages, cell backpacks, and macrophage-backpack conjugates across cell monolayers.

As a test to whether cell backpacks are able to cross a cell monolayer, backpacks alone and those attached to macrophages were incubated in a transwell plate. As shown in FIG.

6, some backpacks were able to cross the cell monolayer, but significantly more could do so when attached to macrophages. The macrophages themselves are able to cross the cell monolayer and the added bulk from the cell backpacks slightly slows their transfer.

In Vitro Ability of Macrophage-Backpack Conjugates to Cross the Blood-Brain Barrier Mice were intoxicated with lipopolysaccharides to induce inflammation in the brain. Twenty-four hours later, macrophage-backpack conjugates were prepared and injected intravenously. Fourteen hours later the mice were sacrificed and the brain was examined for the presence of macrophages, cell backpacks and their conjugates. As shown in FIG. 7, macrophages (labeled green) are found in the brain with co-localization of the cell backpacks (labeled red), clearly indicating the crossover of macrophage-backpack conjugates across the blood brain barrier. When backpacks alone (not attached to macrophages) were administered intravenously, they were not found in the brain.

Other embodiments are within the scope of the following claims.

What is claimed is:

1. A composition for targeted drug delivery comprising:
   a cell capable of crossing a blood-brain barrier; and
   a cell backpack adhered outside the cell to form a cell backpack conjugate, the cell backpack including a polymer patch including a drug, the polymer patch associated with a fractional portion of the cell surface;
   wherein the polymer patch includes:
      a cytophilic layer having a specific affinity for the cell surface and being substantially in contact with the cell surface;
      an exposed layer; and
      one or more functional layers intermediate to the cytophilic layer and the exposed layer, wherein the functional layer contains the drug and includes a magnetic region, wherein the functional layer includes a polyelectrolyte multilayer; and
   a targeting ligand that is a peptide, an antibody, or an aptamer that helps direct macrophages to the brain, wherein the targeting ligand decorates the cell backpack conjugate resulting in a composition that can deliver a pharmaceutical across a blood-brain barrier.

2. The composition of claim 1, wherein the cell is a neutrophil, a monocyte, a macrophage, a mast cell, a dendritic cell, or a mesenchymal stem cell.

3. The composition of claim 1, wherein the cell is a macrophage.

4. The composition of claim 1, wherein the drug is an enzyme.

5. The composition of claim 4, wherein the enzyme is catalase.

6. The composition of claim 1, wherein the drug maintains its activity after crossing the blood-brain barrier.

7. The composition of claim 1, wherein the cytophilic layer includes hyaluronic acid, chitosan, biotin, an antibody, or an adhesive peptide.

8. The composition of claim 1, wherein the cytophilic layer includes a polyelectrolyte multilayer.

9. The composition of claim 1, wherein the exposed layer includes a polyelectrolyte multilayer.

10. The composition of claim 1, wherein the polyelectrolyte multilayer includes poly(allylamine hydrochloride) (PAH).

11. The composition of claim 1, further comprising a magnetic layer between the functional layer and the exposed layer.

12. The composition of claim 1, wherein the polymer patch has lateral dimensions in the range of 1 μm to 250 μm and a thickness in the range of 50 nm to 1 μm.

* * * * *